United States Patent
McAlexander

(10) Patent No.: US 9,335,265 B2
(45) Date of Patent: May 10, 2016

(54) SPECTROGRAPHIC SYSTEM UTILIZING A CHIRPED, PULSED OPTICAL SOURCE

(71) Applicant: Agilent Technologies, Inc., Loveland, CO (US)

(72) Inventor: William I. McAlexander, Redwood City, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 89 days.

(21) Appl. No.: 14/175,950

(22) Filed: Feb. 7, 2014

(65) Prior Publication Data
US 2015/0226667 A1 Aug. 13, 2015

(51) Int. Cl.
| | |
|---|---|
| *G01J 3/42* | (2006.01) |
| *G01N 21/61* | (2006.01) |
| *G01N 21/39* | (2006.01) |
| *G01N 21/59* | (2006.01) |
| *G01N 21/41* | (2006.01) |

(52) U.S. Cl.
CPC .............. *G01N 21/59* (2013.01); *G01N 21/39* (2013.01); *G01N 21/41* (2013.01); *G01J 3/42* (2013.01); *G01N 21/61* (2013.01)

(58) Field of Classification Search
CPC ............. G01J 3/42; G01J 3/45; G01J 3/28; G01J 3/12; G01N 21/3504; G01N 21/39; G01N 21/61; G01N 21/41; G01N 21/59; G02B 21/0064
USPC ............ 356/237.1–241.6, 242.1–243.8, 356/426–431, 600–640
See application file for complete search history.

(56) References Cited

U.S. PATENT DOCUMENTS

| | | | | |
|---|---|---|---|---|
| 3,690,772 | A * | 9/1972 | Endl | 356/408 |
| 4,272,193 | A * | 6/1981 | Eastman et al. | 356/486 |
| 4,792,230 | A * | 12/1988 | Naganuma et al. | 356/450 |
| 5,345,306 | A * | 9/1994 | Ichimura | G01N 21/17 356/451 |
| 5,883,714 | A * | 3/1999 | Jann | G01N 21/88 356/237.2 |
| 5,969,815 | A * | 10/1999 | Toida et al. | 356/484 |
| 6,573,700 | B2 * | 6/2003 | Zhang et al. | 324/96 |
| 7,271,594 | B2 * | 9/2007 | Abreu | G01J 3/42 324/457 |
| 7,433,043 | B2 * | 10/2008 | Birge et al. | 356/450 |
| 8,049,956 | B2 * | 11/2011 | Kong | G02F 1/39 359/330 |
| 8,355,137 | B2 * | 1/2013 | Resch | G02F 1/21 356/450 |
| 8,564,785 | B2 * | 10/2013 | Newbury | G01J 3/453 356/451 |
| 8,687,200 | B2 * | 4/2014 | Lee | G01B 9/02027 250/237 G |
| 8,748,822 | B1 * | 6/2014 | Gerecht | G01J 3/42 250/339.07 |
| 9,030,663 | B2 * | 5/2015 | Braun et al. | 356/432 |
| 2006/0119855 | A1 * | 6/2006 | Li | 356/450 |

* cited by examiner

*Primary Examiner* — Tri Ton
*Assistant Examiner* — Jarreas C Underwood

(57) ABSTRACT

An apparatus and method for measuring the attenuation and dispersion introduced by a sample into an optical signal are disclosed. The apparatus includes a chirped light source, a beam splitter and an optical detector. The beam splitter splits the optical signal generated by the light source into a reference optical signal and a sample optical signal. The sample and reference optical signals are mixed on the detector after the sample optical signal has traversed an experimental sample thus generating a signal having an AC component related to an attenuation and a dispersion introduced by the experimental sample. The optical paths traversed by the reference and sample optical signals between the beam splitter and the detector are chosen such that the reference optical signal and the sample optical signal overlap in time but do not arrive at the optical detector at the same time.

13 Claims, 2 Drawing Sheets

SPECTROGRAPHIC SYSTEM UTILIZING A CHIRPED, PULSED OPTICAL SOURCE

BACKGROUND OF THE INVENTION

Laser absorption spectroscopy that utilizes tunable lasers as the light source is useful in measuring the absorption of samples. In the simplest measurement apparatus the incident light is caused to pass through the sample and is detected by an optical detector. For the case of a strong absorber, the signal at the detector can be small and difficult to measure. Furthermore, the described simple measurement fails to measure the dispersion of the sample.

Heterodyne-based detection systems provide significant improvements over the simple system discussed above. In a heterodyne detection system, the output of the laser is modulated at an RF frequency to create a light component at a slightly different wavelength that provides a reference signal that is mixed with the signal from the sample. This reference signal gives rise to a beat frequency in the detector output. A strong reference signal can generate a beat signal which is easier to detect for instances where the absorption is strong. The beat signal also provides both amplitude and phase information that can be used to provide a measurement of the absorption and dispersion introduced by the sample.

Heterodyne-based receivers that utilize an acoustic optical modulator to generate the second frequency are known to the art. However, these modulators add complexity to the instrument and are limited in the wavelengths that can be generated for the reference beam without repositioning the acoustic optical modulator.

SUMMARY OF THE INVENTION

The present invention includes an apparatus and method for measuring the attenuation and dispersion introduced by a sample into an optical signal. The apparatus includes a chirped light source, a beam splitter and an optical detector. The chirped light source generates a coherent optical signal in the form of a light pulse. The beam splitter splits the optical signal into a reference optical signal and a sample optical signal. The optical detector mixes the sample optical signal and the reference optical signal, after the sample optical signal has traversed an experimental sample and generates a signal having an AC component related to an attenuation and a dispersion introduced by the experimental sample. The reference optical signal traverses a reference optical path characterized by a reference optical path length between the beam splitter and the detector, and the sample optical signal traverses a sample optical path characterized by a sample optical path length between the beam splitter and the detector. The sample optical path length and the reference optical path length are chosen such that the reference optical pulse and the sample optical pulse overlap in time but do not arrive at the optical detector at the same time. The difference in optical path length is chosen such that the AC signal has a non-zero frequency less than the bandwidth of the optical detector.

In one aspect of the invention, the reference optical path is characterized by a first physical length, and the sample optical path is characterized by a second physical length, the first physical length being different from the second physical length. One of the optical paths can optionally include a variable path length element that alters the path length of that path in response to a signal input thereto. The optical path length of the variable optical path element may be varied during a pulse generated by the chirped light source.

In another aspect of the invention, the optical detector includes first and second optical detectors and a beam splitter. The beam splitter splits the reference optical signal into first and second reference detector signals and splits the sample optical signal into first and second sample detector signals. The first reference detector signal and the first sample optical signal are mixed on the first optical detector to generate a first electrical detector signal. The second reference detector signal and the second sample optical signal are mixed on the second optical detector to generate a second electrical detector signal. The second electrical detector signal has an AC component that is 180 degrees out of phase with respect to an AC component of the first electrical detector signal. A signal combiner combines the first and second electrical detector signals to produce a detector output signal in which any DC component common to both the first and second electrical detector signals is eliminated from the detector output signal.

In another aspect of the invention, a signal analyzer measures the frequency of the AC component.

DETAILED DESCRIPTION OF THE PREFERRED EMBODIMENTS OF THE INVENTION

Figure 1:
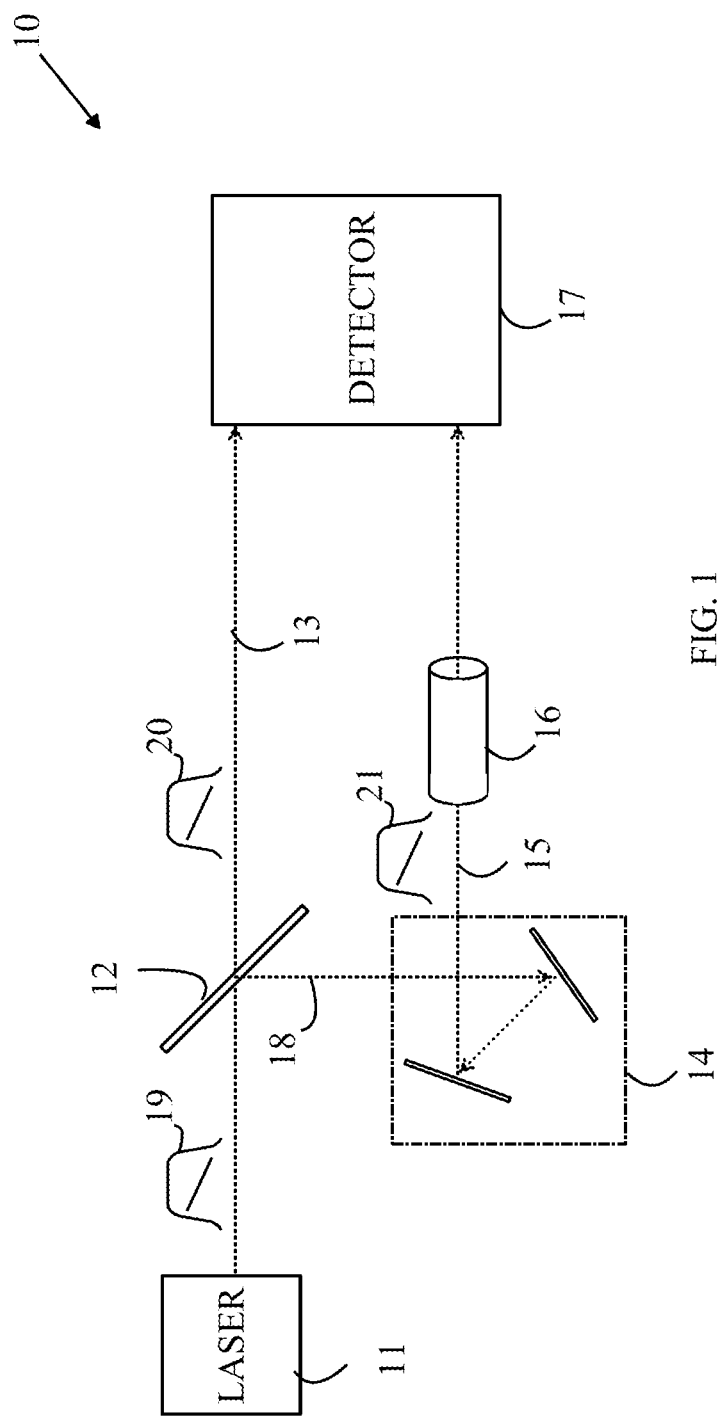
FIG. 1 illustrates one embodiment of a spectrometer according to the present invention.

The present invention is based on the observation that some lasers exhibit a frequency shift when pulsed such that the wavelength of light varies in a continuous manner over the pulse. Quantum cascade lasers exhibit this behavior. Refer now to FIG. 1, which illustrates one embodiment of a spectrometer according to the present invention. In spectrometer 10, a pulse 19 from a laser 11 is split into first and second pulses that will be referred to as reference pulse 20 and sample pulse 21 by beam splitter 12. The reference pulse traverses path 13, and the sample path travels along paths 18 and 15, passing through a sample 16 that is to be characterized. In this embodiment, the path between beam splitter 12 and detector 17 that includes segment 13 is shorter than the path that includes path 18 between beam splitter 12 and detector 17. Hence, the sample pulse arrives at detector 17 after the reference pulse; however the delay is set such that the reference and sample pulses overlap in time at detector 17. The amount of the delay can be adjusted by setting the distance between the mirrors in delay path 14. After leaving the sample, sample pulse 21 is mixed with the light from reference pulse 20 in detector 17 to produce a heterodyne signal that provides information about the absorption and dispersion of sample 16.

The wavelength of the pulses from the laser decreases with time, and hence, the frequency of the laser light increases with time. For the purposes of this discussion, it will be assumed that the increase in laser frequency is linear, i.e., $$\omega(t) = \omega_0 + Rt,$$

where
$\omega_0$ is the frequency of the laser light at the beginning of the pulse and R is a constant that measures the rate of change of the frequency. Denote the delay between the reference and sample paths by $\Delta t$. To simplify the notation, define $t=0$ as the time that the reference pulse first arrives at detector 17. To further simplify the discussion, it will be assumed that the sample does not significantly alter the optical path between beam splitter 12 and detector 17. The frequency of the reference beam at the detector as a function of time is given by $$\omega_r(t)=\omega_0+Rt.$$

and the frequency of the sample beam at the detector is given by $$\omega_s(t)=\omega_0+R(t+\Delta t)$$

Denote the amplitude and phase of the reference signal at detector 17 by $A_r$ and $\phi_r$, respectively. Similarly, denote the amplitude and phase of the sample signal at detector 17 by $A_s$ and $\phi_s$, respectively. Then the signal at the detector when these two signals mix is proportional to $$D(T)=A_r^2+A_s^2+2A_rA_s\cos((R\Delta t)t+(\phi_r-\phi_s)) \quad (1)$$

Hence, assuming the detector has sufficient frequency response to measure the amplitude and phase of a signal at a frequency of $(R\Delta t)$, the absorption and dispersion introduced by the sample can be determined.

In one exemplary embodiment, a laser having a frequency that increases by 37 MHz/ns was utilized. By utilizing a delay of 0.5 ns between the reference and sample pulses, the AC term in Equation (1) was 21 MHz which is within the bandwidth of commercially available optical detectors. Finding the optimal detector bandwidth depends on the width of the pulse, the availability of detectors, and the chirp of the laser source. Ideally the detector is fast enough to capture multiple cycles of the beat frequency, as more cycles lead to better precision on the determination of the beat signal amplitude and frequency. However, a higher frequency beat signal requires a faster detector which typically introduces more noise. A tradeoff exists that must be evaluated for the components at hand.

Figure 2:
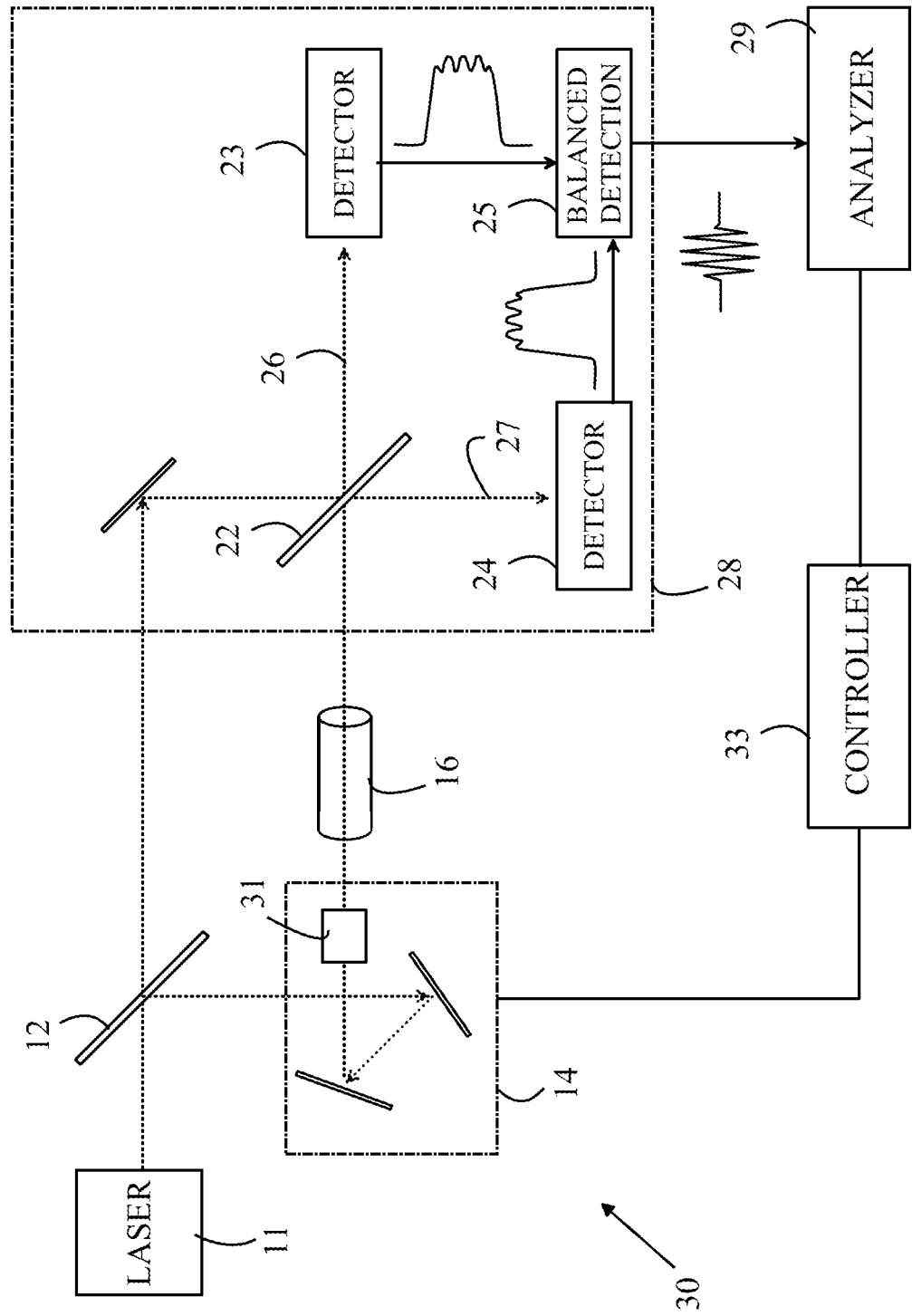
FIG. 2 illustrates another embodiment of a spectrometer according to the present invention.

While a simple single photodetector could be utilized for detector 17, the large amplitude constant term, $A_r^2+A_s^2$, leads to signal-to-noise problems in such a simple detector. Accordingly, a balanced detector arrangement in which the constant terms are eliminated is preferred. Refer now to FIG. 2, which illustrates another embodiment of a spectrometer according to the present invention. To simplify the following discussion, those elements of spectrometer 30 that serve functions analogous to those served by corresponding elements in spectrometer 10 discussed above have been given the same numeric designations and will not be discussed in detail here. In spectrometer 30, detector 17 discussed above has been replaced by detector 28 that removes the constant terms discussed above. Detector 28 splits the reference and sample beams with beam splitter 22. The split beams are directed to detectors 23 and 24, respectively. Beam splitter 22 introduces a 180 degree phase shift between beams 26 and 27. Hence, when the signals generated by detectors 23 and 24 are subtracted in balanced detector 25, the constant terms are eliminated leaving the AC signal.

The frequency of the AC signal from balanced detector 25 is determined by the difference in transit time between the reference pulse and the sample pulse combined with the inherent chirp of the laser source. This delay depends on the delays that have intentionally been introduced and any delay introduced by the sample itself. Conversely, by measuring the frequency of the AC signal and knowing the chirp of the laser source, the total delay between the two signals can be determined. If this frequency is also measured without the sample, any delay introduced by the sample can be deduced. Such sample related delays are the result of dispersion in the sample. If the sample related delay corresponds to a difference in path length of less than one wavelength, the difference is reflected in the phase of the AC signal. If the delay is larger than this delay, the phase difference will not be determinative of the delay. This latter case can be detected by measuring the AC signal using a signal analyzer 29.

The above-described embodiments assumed that the frequency of the light generated by the laser increases or decreases linearly with time during the pulse. It is advantageous to use as long a pulse as possible so as to sweep as large a wavelength band as possible, and hence, characterize the sample over a large range of wavelengths. At some point, the frequency of the laser light will cease to change linearly with time into the pulse. At this point, the frequency of the AC signal will no longer be constant. However, by measuring the frequency, amplitude, and phase of the AC signal, the signal can still be utilized to characterize the sample, and hence, extend the range of the instrument. Furthermore, the laser source pulses can be tuned to different center wavelengths to achieve even greater instrument range.

In the above-described embodiments, the difference in the optical path between the reference and sample pulse paths is set to provide a particular target frequency or frequency range for the AC signal generated by the detector that measures the mixed signals. This difference in optical paths is held constant during the measurement. In the above described embodiments the optical delay is introduced by adjusting the positions of the mirrors shown in delay path 14. However, other variable optical path elements for adjusting the difference in the length of the paths could be utilized. For example, optical elements that have an index of refraction that changes as a function of applied voltage are known to the art. In addition, optical elements that alter the optical path length by mechanically moving an element such as a prism can also be utilized.

In one aspect of the invention, the delay path can include a variable index of refraction element 31 having an index of refraction that is varied in response to a signal from controller 33. In such an embodiment, the optical path difference can be varied during the pulse to compensate for a non-linearity in the frequency output of the laser during the pulse.

The above-described embodiments of the present invention utilize a laser having an output pulse whose frequency changes as a function of time as measured from the start of the pulse. However, other "chirped" sources could be utilized. For the purpose of this discussion, a "chirped optical source" is any optical source that generates a coherent optical signal whose optical frequency changes as a function of time as measured from the start of the pulse.

In the above-described embodiments, the difference in optical path lengths between the reference and sample optical paths is generated by utilizing a longer physical path between the chirped optical source and the detector. However, embodiments in which the reference optical path has the longer optical path length could also be constructed. The difference in optical path length can be generated by having different physical path lengths and/or having an element in one of the paths that increases the average index of refraction along the longer path.

In the above described embodiments various detectors are used to convert an optical signal to an electrical signal. For the purposes of this discussion, an optical detector is defined to be an element that generates an electrical signal having an amplitude determined by the intensity of a light signal that is applied to a surface of the detector. Photodiodes are examples of such detectors; however, other "square law detectors" such as phototransistors could also be utilized.

The above-described embodiments of the present invention have been provided to illustrate various aspects of the invention. However, it is to be understood that different aspects of the present invention that are shown in different specific embodiments can be combined to provide other embodiments of the present invention. In addition, various modifications to the present invention will become apparent from the foregoing description and accompanying drawings. Accordingly, the present invention is to be limited solely by the scope of the following claims.

What is claimed is:

1. An apparatus comprising:
a chirped light source that generates an optical signal;
a beam splitter that splits said optical signal into a reference optical signal and a sample optical signal;
a detector that mixes said sample optical signal and said reference optical signal, after said sample optical signal has traversed an experimental sample and generates a signal having an AC component related to an attenuation and a dispersion introduced by said experimental sample, wherein said reference optical signal traverses a reference optical path characterized by a reference optical path length between said beam splitter and said detector, and wherein said sample optical signal traverses a sample optical path characterized by a sample optical path length between said beam splitter and said detector, said sample optical path length and said reference optical path length being chosen such that said reference optical signal and said sample optical signal overlap in time but do not arrive at said detector at the same time.

2. The apparatus of claim 1 wherein said reference optical path is characterized by a first physical length and said sample optical path is characterized by a second physical length, said first physical length being different from said second physical length.

3. The apparatus of claim 1 wherein said detector is characterized by a detection bandwidth and wherein said sample optical path length and said reference optical path length are chosen such that said AC component has a frequency less than said detection bandwidth.

4. The apparatus of claim 1 wherein one of said reference optical path and said sample optical path includes a variable optical path element whose optical path length is varied as a function of a signal input to said variable optical path element.

5. The apparatus of claim 4 wherein said optical path length of said variable optical path element is varied during a pulse generated by said chirped light source.

6. The apparatus of claim 1 wherein said detector comprises a first optical detector and a second optical detector.

7. The apparatus of claim 6 wherein said detector further comprises:
a beam splitter that splits said reference optical signal into first and second reference detector signals and that splits said sample optical signal into first and second sample detector signals, said first reference detector signal and said first sample optical signal being mixed on said first optical detector to generate a first electrical detector signal and said second reference detector signal and said second sample optical signal being mixed on said second optical detector to generate a second electrical detector signal, said second electrical detector signal having an AC component that is 180 degrees out of phase with respect to an AC component of said first electrical detector signal; and
a signal combiner that combines said first and second electrical detector signals to produce a detector output signal such that any DC component common to both said first and second electrical detector signals is eliminated from said detector output signal.

8. The apparatus of claim 1 wherein said AC component comprises a plurality of frequencies having different amplitudes and said apparatus further comprising a signal analyzer that measures said frequencies and amplitudes of said AC component.

9. The apparatus of claim 8 wherein one of said reference optical path and said sample optical path includes a variable optical path element whose optical path length is varied as a function of a signal input to said variable optical path element, said input signal being generated in response to said frequency of said AC component.

10. A method for measuring an attenuation and a dispersion characterizing a sample, said method comprising:
splitting a chirped optical source into a reference optical signal and a sample optical signal;
causing said sample optical signal to traverse said sample prior to arriving at an optical detector;
combining said sample optical signal and said reference optical signal on said optical detector to generate a signal having an AC component related to said attenuation and said dispersion, wherein said reference optical signal and said sample optical signal overlap in time upon arriving at said optical detector but do not arrive at said optical detector at the same time and
measuring an amplitude and a phase of said AC component.

11. The method of claim 10 wherein said reference optical signal traverses a first optical path characterized by a first path length before arriving at said optical detector and wherein said sample optical signal traverses a second optical path characterized by a second path length to reach said optical detector, said first path length being different from said second path length.

12. The method of claim 11 wherein one of said first and second optical paths includes a variable optical path element whose optical path length is varied as a function of a signal input to said variable optical path element.

13. The method of claim 12 wherein said optical path length of said variable optical path element is varied during said reference optical signal.

* * * * *

UNITED STATES PATENT AND TRADEMARK OFFICE
CERTIFICATE OF CORRECTION

PATENT NO.        : 9,335,265 B2
APPLICATION NO.   : 14/175950
DATED             : May 10, 2016
INVENTOR(S)       : William I. McAlexander It is certified that error appears in the above-identified patent and that said Letters Patent is hereby corrected as shown below:

In the specification,

In column 3, line 15, delete "$D(T) = A_r^2 + A_s^{2+} 2A_r A_s \cos((R\Delta t)t + (\phi_r - \phi_s))$" and insert -- $D(T) = A_r^2 + A_s^2 + 2A_r A_s \cos((R\Delta t)t + (\phi_r - \phi_s))$ --, therefor.

Signed and Sealed this
Nineteenth Day of July, 2016

Michelle K. Lee
*Director of the United States Patent and Trademark Office*